United States Patent [19]
Shepherd et al.

[11] Patent Number: 4,883,484
[45] Date of Patent: Nov. 28, 1989

[54] DELIVERY DEVICE

[76] Inventors: Michael T. Shepherd, Coopers Animal Health Limited Berkhamsted Hill, Berkhamsted, Hertfordshire, England; Scott R. Edwards, 71, Epping Road, North Ryde, New South Wales, 2113, Australia

[21] Appl. No.: 127,757

[22] Filed: Dec. 2, 1987

[30] Foreign Application Priority Data

Jun. 17, 1986 [GB] United Kingdom ................. 8614716
Jul. 15, 1986 [AU] Australia ............................ PH 06936
Nov. 3, 1987 [EP] European Pat. Off. ........ 87309709.1

[51] Int. Cl.⁴ ............................................ A61M 31/00
[52] U.S. Cl. .................................... 604/891.1; 604/57; 424/438
[58] Field of Search .................... 604/890.1, 891.1, 48, 604/57, 104–107, 174, 175; 424/430, 432, 438, 443, 439

[56] References Cited

U.S. PATENT DOCUMENTS

| 3,844,285 | 10/1974 | Laby ................................ 604/890.1 |
| 3,993,058 | 11/1976 | Hoff ....................................... 604/57 |
| 4,326,522 | 4/1982 | Guerrero et al. ..................... 604/57 |
| 4,416,659 | 11/1983 | Simpson et al. ...................... 604/57 |
| 4,585,451 | 4/1986 | Millar ................................. 424/432 |
| 4,623,330 | 11/1986 | Laby et al. ........................... 604/230 |
| 4,623,345 | 11/1986 | Laby ................................ 604/890.1 |
| 4,687,480 | 8/1987 | Laby et al. ........................... 604/105 |

FOREIGN PATENT DOCUMENTS

| 0079724 | 5/1983 | European Pat. Off. . |
| 0174865 | 3/1986 | European Pat. Off. . |
| WO86/00519 | 1/1986 | PCT Int'l Appl. ............. 604/890.1 |
| 1603970 | 12/1981 | United Kingdom . |
| 2152373 | 8/1985 | United Kingdom ............ 604/890.1 |

Primary Examiner—Stephen C. Pellegrino
Assistant Examiner—Ralph Lewis
Attorney, Agent, or Firm—Donald Brown; Robert T. Gammons

[57] ABSTRACT

An intraruminal device has hinged wings (6) which lie along the body of the device during administration to the animal but which are urged outwardly by a spring (14) acting on a piston (12) shortly thereafter. The wings (6) are locked in the extended position: the piston (12) prevents them returning to the starting position, and T-bars (10) prevent them continuing to an "arms-over-head" position.

The locking means may comprise a latch. The spring (14) may be replaced by a water-swellable polymer which expands on contact with rumen fluids.

The device is used to administer drugs or minerals to the rumen of a ruminant over a prolonged period.

18 Claims, 2 Drawing Sheets

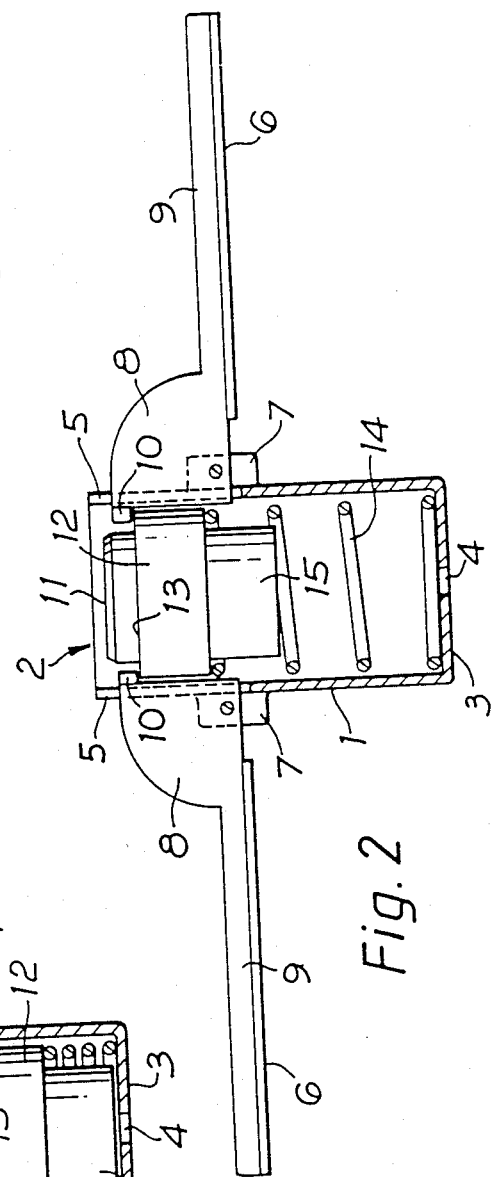
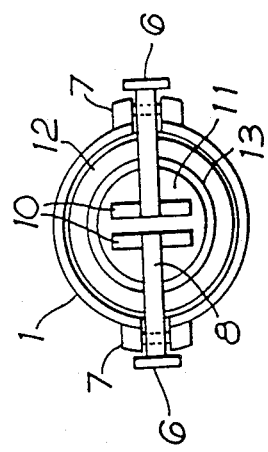
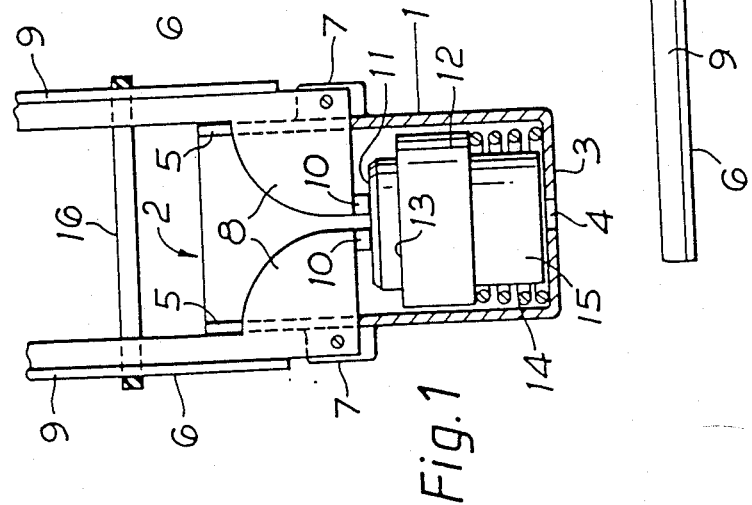

DELIVERY DEVICE

This invention relates to a delivery device.

It is desirable to administer medicaments such as drugs and trace minerals (hereinafter generically referred to as "drugs") to ruminants via the reticulo-rumen ("rumen") of the animal. A solution of the formulated drug may be injected directly into the rumen through the animal's flank. Alternatively, the drug can be administered in the form of a bolus-like artefact which is dispensed orally and lodges in the rumen, thereafter releasing the drug into the rumen at a controlled rate. Several methods have been proposed whereby the article may be suitable for passage through the animal's mouth and esophagus but may still be retained within the rumen without being regurgitated by the animal. One such device relies simply on having a sufficiently dense weight of, for example, steel so that the device is retained in the rumen by gravity. A different device, such as is disclosed in EP-A-174 865, has a tubular body with projecting wings which are hinged to the body. The wings are collapsed against the body when given to the animal, but extend outwardly and away from the body once in the rumen to provide a device of such a size and shape that it cannot easily be regurgitated.

Devices of the latter type have been found, in use, to be regurgitated to an undesirable extent. It is an object of the present invention to provide an improved device of this type. Devices in accordance with the invention may be used in technical areas other than that described above, for example to deliver a bactericide at a controlled rate to an enclosed tank in a water treatment system, or wherever it is desired to release an active agent in an inaccessible enclosure.

One aspect of the present invention provides a device adapted to be retained in a selected bounded location, the device comprising: a main portion; at least one elongate member hingedly attached thereto and movable relative thereto between a compact position wherein the spread of the device is minimized and an extended position wherein the spread of the device is maximized; biasing means to bias the elongate member to the extended position; and a locking means to lock the elongate member in the extended position.

Preferably, the device is an intraruminal depot wherein:

the main portion comprises an elongate body for containing and progressively releasing a veterinary substance;

there is a plurality of the said elongate members, each constituted by a respective wing being pivotally attached at one end thereof to a leading edge of the body, and being resiliently biased to pivot from the said compact position wherein the wing lies alongside the body for passage down the esophagus of an animal to the said extended position wherein the wing projects laterally outwards from the body thereby retaining the device in the rumen; and the locking means are operative between each wing and the body for locking the wings in said extended positions and preventing any subsequent pivotal movement thereof.

Suitably there are two said elongate members integrally moulded into a unitary wing structure.

Conveniently, the biasing means comprises a compression spring.

Alternatively, the biasing means may comprise a pressurized gas-filled chamber or a chamber adapted to increase in pressure due to inward osmosis of fluid from the rumen.

The elongate member is preferably substantially rigid. In prior art devices, "creep" of the flexible elongate members during storage in the compact position has caused permanent deformation thereof, resulting in regurgitation of the device because the fully extended position is not attained or maintained.

The elongate member may be formed separately from the main portion of the device and may be hinged thereto by any suitable hinge mechanism. Preferably, however, the elongate member and the main portion are of unitary construction, suitably of some appropriate plastics material, and the hinged attachment comprises a flexible portion of the plastics material. Suitably, there is a stop means to prevent hinged movement of the elongate member beyond the said extended position.

Preferably, the device comprises a releasable securing means to secure the elongate member in the compact position. The elongate member may, when in the compact position, be accommodated in a complementary channel in the body of the device.

In one main embodiment, the main portion is cylindrical and the biasing means comprises a piston movable within the cylindrical main portion. Suitably the compression spring acts on the piston, thereby to bias indirectly the elongate member, and preferably the piston comprises a first surface adapted to bear on the elongate member to bias it as said and a second surface constituting a part of the locking means. Conveniently, the second surface is substantially parallel to the direction of motion of the piston. Advantageously, the elongate member and the main portion are formed of a plastics material and are of unitary construction, the said hinged attachment comprising a flexible portion of the plastics material.

In a second main embodiment, there are two elongate members hinged together at a central location and the device comprises a cradle bridging the central location and being hinged at either end to a respective elongate member. Preferably, the compression spring mentioned above is provided between the cradle and the central location which biases the elongate members to the outwardly extended position. Suitably, the cradle of the unitary wing structure is mounted on a bridge extending across the leading end of the body. Advantageously, the locking means comprises a latch mechanism operative between each elongate member and the cradle of the unitary structure or the bridge. Preferably, the locking means comprises a barb on the elongate member cooperating with a ramp surface provided on the cradle or bridge, or vice versa.

In a third main embodiment, the depot contains a swellable material which is adapted to swell on contact with ruminal fluids and to function as the said biasing means and (optionally) as the said locking means. Thus, the swellable material may take the place of the compression spring referred to above, with the locking means still comprising the side of a piston (as in the first embodiment above) or a latch mechanism (as in the second embodiment above). Alternatively, the continued pressure of the swollen material may directly act to lock the wings in position, although this is usually less satisfactory.

Suitable swellable materials are known as vehicles for drugs, particularly in intraruminal depots. In the present invention the material may in part act in the known way, namely slowly extruding through an orifice for subsequent dispersion into the rumen, or it may be provided separately from the matrix in which the drug is carried. Suitable materials include those disclosed in U.S. Pat. Nos. 3,641,237, 3,660,071 and U.S. Pat. No. 4,451,635. Such polymers can be obtained from Tyndale Plains-Hunter Ltd. Princeton, N.J., U.S.A.

As discussed above, devices in accordance with the invention are particularly suitable for use as or with intra-ruminal drug delivery devices, and further aspects of the invention provide such a particularly adapted device and a method of delivering a drug (as herein defined) to a ruminant using such a device.

The device may itself incorporate the drug formulation to be dispensed, or may be attached to a suitable chamber in which the drug formulation is contained. The drug may be released in a controlled manner by any suitable technique. For example, the formulation may be adapted to be slowly eroded by the aqueous conditions within the rumen or, in an embodiment particularly suited for pulsed release of a drug, the device may comprise a magnesium alloy portion which is eroded within the rumen such that discrete lumps of drug formulation are sequentially released into the rumen for solution and absorption. Alternatively, the device may be attached to a chamber in which a spring-biased piston urges drug formulation towards an opening, allowing contact with, and hence erosion or dissolution by, the rumen fluids, for example a system as described in U.K. Patent Specification No. 1,603,970 (CSIRO).

"Drugs" such as anthelmintics (for example oxfendazole), trace elements (such as cobalt, copper and selenium), growth promotants (such as monensin and ICI M-139603) and anti-bloat surfactants may be administered by means of a device in accordance with the invention.

So that the invention may be more readily understood and so that preferred features may become apparent, two particular embodiments of the invention will now be described by way of example and with reference to the accompanying drawings, in which:

FIG. 1 is a vertical longitudinal sectional view of a first embodiment, with the elongate members thereof in the compact position;

FIG. 2 is a view corresponding to FIG. 1, but with the elongate members in the extended position;

FIG. 3 is a top view of the device as shown in FIG. 1;

Figures 4, 5:
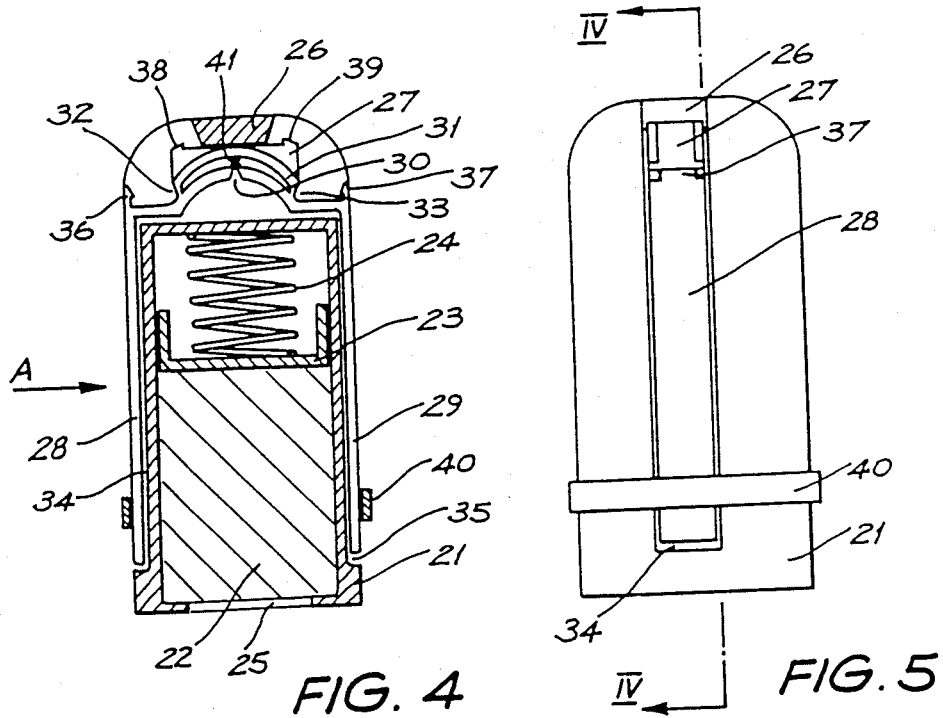
FIG. 4 is a longitudinal section of a second embodiment, taken along line IV—IV in FIG. 5.
FIG. 5 is a side view of the device of FIG. 4, looking in the direction of arrow A.

The device comprises a tubular body 1 having an open end 2 and a substantially closed opposed end 3 provided with a small orifice 4 therein. Diametrically opposed longitudinal slits 5 which are open at the top are provided in the upper one third of the body 1 and accommodate respective wings 6. By means of respective hinge blocks 7, the wings 6 are hingedly attached to the body 1 about respective parallel axes extending tangentially to the circumference of the body 1. The hinge blocks 7 are joined to the outside of the body 1 towards the bottom of the slits 5.

Each wing 6 has a quadrant-shaped portion 8, the hinge axis of the wing 6 passing through adjacent the arc centre thereof, and an elongate portion 9 of T-section which, in the compact position shown in FIG. 1, extends upwardly parallel to the axis of the tubular body 1. The corner of the quadrant-shaped portion 8 remote from the hinge axis and adjacent to the elongate portion 9 is provided with a downwardly depending T-bar 10, the top of the "T", as can most readily be seen in FIG. 3, extending transversely to and adjacent the longitudinal axis of the tubular body 1.

The two T-bars 10 bear on the top surface 11 of a piston 12 arranged for longitudinal motion within the tubular body 1. The top surface 11 has a smaller diameter than the internal diameter of the body 1 and is raised with relation to the remainder of the piston 12, thus forming an annular step 13 in the piston 12. Under the lower surface of the piston 12 there is a compression spring 14 which acts against the end wall 3 of the body 1 to urge the piston 12 upwardly. To assist the spring 14 in this action, the piston 12 is provided with a downwardly depending boss 15 having a diameter less than that of the main portion of the piston 12, such that the compression spring 14 is arranged concentrically around the boss 15. The orifice 4 allows the pressure in the space vacated by the piston 12 to equalize, so that the action of the spring is not opposed by external pressure on the top surface of the piston, but is necessary only if the piston has a tight fit with the body 1.

In this particular embodiment, the body 1, wings 6 and piston 12 are all formed of a relatively rigid lightweight plastics material such as PVC, polystyrene, HDPE, polycarbonate or, preferably, acrylic. Again in this particular embodiment, the main body is approximately 5.5 cm, the diameter of the body 1 is about 3 cm and the elongate portions 9 of the wings 6 are each about 9 cm long. In use, the device illustrated in the accompanying drawings is attached to a suitable chamber for the drug to be delivered, as discussed in general terms above, with such chamber usually being provided at the top of the device as shown in FIG. 1. The wings 6 are held against the action of the spring 14 by means of a band 16, tape or tube formed of a material which will disintegrate or dissolve in the rumen of the animal, for example cardboard. The device is then administered in a known manner to the animal and, after a predetermined time in the rumen, the band or tape will disintegrate or dissolve, whereupon the compression spring 14 will force the piston 12 upwardly (as shown in FIG. 1) along the body 1, thereby similarly forcing upwardly and outwardly the quadrant-shaped portion 8 of the wings 6. Thus, it can be seen that the wings 6 will be pushed outwardly to a position at which they are substantially at right angles to the length of the body 1, as is illustrated in FIG. 2. The T-bars 10 of the quadrant-shaped portion 8 of the wings 6 cannot pass through the slits 5 in the body 1 and thereby prevent the wings from passing beyond the fully extended position. In prior art devices, the movement of the wings beyond the fully extended position has resulted in regurgitation of the device.

It can be seen that, when the wings 6 are in the fully extended position shown in FIG. 2, the side of the piston 12 prevents them from returning to the compact position shown in FIG. 1, either by virtue of the T-bar 10 engaging the step 13 of the piston 12 or by virtue of the quadrant-shaped portion 8 engaging the main, that is to say full diameter, portion of the piston 12, depending upon the precise relative dimensions of the components.

In the embodiment illustrated in the drawings, the wings 6 are formed separately from the body 1 and are hinged thereto by means of a conventional hinge arrangement. However, for ease and economy of manufacture, it is preferable for the wings 6 and the body 1 to be unitarily formed in a single moulding operation, the hinged movement between them being provided by a flexible portion of the constituent material. It is to be noted that, in contrast with known devices of this general type, such a flexible hinge portion is not in itself responsible for keeping the wings 6 in the fully extended position in the rumen. Instead, the strain is taken by direct engagement of the wings 6 on the piston 12, the surfaces which engage one another being substantially parallel to the direction of action of the spring biasing means 14. This construction has been found to extend significantly the life of the flexible hinge portion; clearly, a weakened hinge portion may result in the wing 6 dropping off the body 1, in which case the device will probably be regurgitated or otherwise ejected from the rumen before all of the drug has been delivered.

Other means of locking the wings 6 to prevent them returning to the compact position are within the scope of the present invention. For example, the T-bar portion 10 of the wings 6 may snap into a hook arrangement provided on the interior wall of the body 1, so that direct engagement with the piston 12 is unnecessary. This in turn allows the piston arrangement to be reversed, so that the compression spring 14 bears upon an abutment, say halfway up the body 1, and forces a piston downwardly (as shown in FIGS. 1 and 2), thus pulling, rather than pushing, the wings 6 to the fully extended position. Alternatively, a tension spring may be used to achieve the same effect.

The number of wings 6, the angle which they form with the body when in the extended position and their cross-section may be varied according to the conditions of use. For example, a cross-section of "I" or keyhole configuration may be used.

Figure 6:
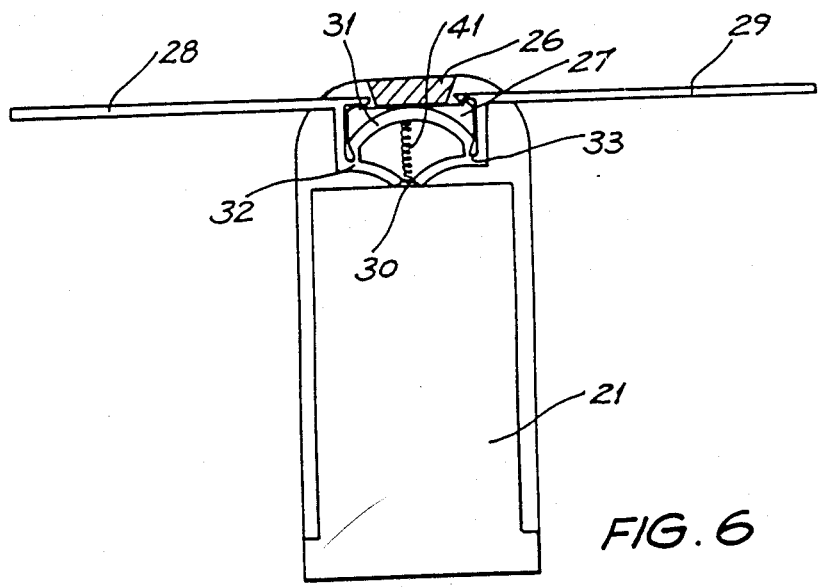
FIG. 6 is a longitudinal section corresponding to FIG. 4, but with various internal components omitted from the drawing, showing the wings in the extended position.

Referring now to FIGS. 4 to 6, the second embodiment comprises a cylindrical body 21 containing a matrix 22 comprising a veterinary substance, a plunger 23 and a spring 24 operative between one end of the body and the plunger 23 for forcing matrix 22 out of an aperture 25 provided in a trailing end of the body. The body also comprises a bridge 26 at a leading end of the body to which is attached a unitary wing assembly 27. The wing assembly is integrally moulded from a plastics material and comprises two wing portions 28, 29 hingedly connected at a central hinge 30. A cradle 31, also integrally moulded with the wing structure, is hinged to respective wing portions at hinges 32, 33. Each wing portion 28, 29 has a right angle bend to enable the wing to be stowed alongside the body in a respective channel 34, 35. Close to the right angle bend, each wing portion has a respective barb 36, 37 which engages with a corresponding ramp surface 38, 39 provided on the cradle.

In order to hold the wing portions 28, 29 stowed against the side of the body, a band 40 formed of a water-soluble plastics material is provided around the body. This resists extension of the wing portions 28, 29 under the action of a spring 41 interposed between the cradle and the central hinge.

The depot being the top may be used as follows. Firstly, the depot in the configuration shown in FIGS. 4 and 5 is administered leading edge (the leading edge being the top, as shown in the drawings) first down the esophagus of the animal until it rests in the rumen. Once in the rumen, the fluids present rapidly dissolve the band 40 and free the wing portions 28, 29. Under the action of the compressed spring 41, the wing portions move to an extended position as shown in FIG. 6 as the central hinge 30 is forced downwardly. In the extended position, the barbs 36, 37 become latched with the ramp surfaces 38, 39, so preventing retraction of the wing portions towards the stowed position. Moreover, the abutment of the wing portions against the cradle prevents further movement of the wing portions towards an "arms above head" position (where the wing portions extend above the leading end of the body). Thus, the wing portions are locked against any further pivotal movement, thereby effectively retaining the depot in the rumen.

In a known manner, the veterinary substance present in the matrix 22 becomes softened by extrusion through the apertures 25 under the action of the spring 24 as the exposed end of the matrix becomes softened by contact with rumen fluids. In this way, a progressive release of the veterinary substance into the rumen is achieved until the matrix is used up.

The compression spring 24 (or 14, in the first embodiment) may be replaced by a piece of water-swellable material, preferably contained in a small tube, which swells on contact with rumen fluids and thus forces the wings open.

We claim:
1. An intra-ruminal depot adapted to be retained in the rumen of a ruminant animal which comprises:
    a main portion comprising an elongate body for containing and progressively releasing a veterinary substance;
    a plurality of elongate members hingedly attached thereto and movable between a compact position wherein the spread of the depot is minimized and an extended position wherein the spread of the device is maximized, each elongate member being constituted by a respective wing pivotally attached at one end thereof to a leading end of the body, each wing being resiliently biased to pivot from the said compact position wherein the wing lies alongside the body for passage down the esophagus of the animal to the said extended position wherein the wing projects laterally outwards from the body, thereby retaining the depot in the rumen;
    biasing means operatively mounted on the body to bias the elongate members to the extended position;
    stop means operatively mounted on the body to prevent hinged movement of each elongate member beyond the said extended position; and
    locking means carried on the body and operative between each elongate member and the body for locking the wings in the said extended position and preventing any subsequent pivotal movement away from the said extended position.

2. A device according to claim 1 wherein there are two said elongate members integrally moulded into a unitary wing structure.

3. A device according to claim 1 wherein the biasing means comprises a compression spring operative between the body and the wings.

4. A device according to claim 1 additionally comprising a releasable securing means to secure each elongate member in the compact position.

5. A device according to claim 3 wherein the main portion is cylindrical and the biasing means comprises a spring biased piston movable within the cylindrical main portion.

6. A device according to claim 1 wherein each elongate member is substantially rigid.

7. A device according to claim 1 wherein the main part is cylindrical and the biasing means comprises a compression spring acting on a piston movable within the cylindrical main portion thereby to bias indirectly the elongate members.

8. A device according to claim 7 wherein the piston comprises a first surface at the leading end of the piston adapted to bear on the elongate member to bias it and a second surface on the cylindrical side of the piston constituting a part of the said locking means.

9. A device according to claim 8 wherein the second surface is substantially parallel to the direction of motion of the piston.

10. A device according to claim 1 wherein the elongate members and the main portion are formed of a plastics material and are of unitary construction, the hinged attachments between the elongate members and body comprising a flexible portion of the plastics material.

11. A device according to claim 1 wherein there are two elongate members hinged together at a central location and the device comprises a cradle bridging the central location and being hinged at either end to a respective elongate member.

12. A device according to claim 1 wherein there are two elongate members hinged together at a central location and the device comprises a cradle bridging the central location and being hinged at either end to a respective elongate member characterized in that a compression spring is provided between the cradle and the central location which biases the elongate members to the outwardly extended position.

13. A device according to claim 12 wherein the cradle of the unitary wing structure is mounted on a bridge extending across the leading end of the body.

14. A device according to claim 13 wherein the locking means comprises a latch mechanism operative between each elongate member and the cradle of the said unitary structure or the bridge.

15. A device according to claim 14 wherein the locking means comprises a barb on the elongate member cooperating with a ramp surface provided on the cradle.

16. A device according to claim 14 wherein the locking means comprises a barb on the elongate member cooperating with a ramp surface provided on the bridge.

17. An intra-ruminal drug delivery system comprising a device according to claim 2, and a drug formulation.

18. A system according to claim 17 additionally comprising a cylindrical body containing the drug formulation, the cylindrical body being adapted for controlled release of the formulation under predetermined conditions.

* * * * *